(12) United States Patent
Jayaraman et al.

(10) Patent No.: US 12,383,192 B2
(45) Date of Patent: Aug. 12, 2025

(54) PRESSURE ULCER PREVENTION SYSTEM

(71) Applicant: Georgia Tech Research Corporation, Atlanta, GA (US)

(72) Inventors: Sundaresan Jayaraman, Atlanta, GA (US); Sungmee Park, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 905 days.

(21) Appl. No.: 16/979,200

(22) PCT Filed: Mar. 16, 2019

(86) PCT No.: PCT/US2019/022650
§ 371 (c)(1),
(2) Date: Sep. 9, 2020

(87) PCT Pub. No.: WO2019/178583
PCT Pub. Date: Sep. 19, 2019

(65) Prior Publication Data
US 2020/0405217 A1    Dec. 31, 2020

Related U.S. Application Data

(60) Provisional application No. 62/644,044, filed on Mar. 16, 2018.

(51) Int. Cl.
*A61B 5/00* (2006.01)
*A61F 5/01* (2006.01)
(Continued)

(52) U.S. Cl.
CPC ............ *A61B 5/447* (2013.01); *A61B 5/6892* (2013.01); *A61B 5/7267* (2013.01);
(Continued)

(58) Field of Classification Search
CPC ..... A61B 5/447; A61B 5/6892; A61B 5/7267; A61B 5/7275; A61B 5/746;
(Continued)

(56) References Cited

U.S. PATENT DOCUMENTS

| | | | |
|---|---|---|---|
| 5,033,291 A | * | 7/1991 | Podoloff ................. G01L 1/205 73/172 |
| 9,635,897 B2 | | 5/2017 | Prust et al. |

(Continued)

FOREIGN PATENT DOCUMENTS

| | | |
|---|---|---|
| CN | 102497844 A | 6/2016 |
| EP | 1987806 A2 | 11/2008 |
| WO | 2018/195444 A1 | 10/2018 |

*Primary Examiner* — Andrey Shostak
(74) *Attorney, Agent, or Firm* — Meunier Carlin & Curfman LLC

(57) ABSTRACT

Disclosed are various embodiments for a pressure ulcer monitoring and prevention system. A fabric-based sensing component with a pressure sensing component and/or a moisture sensing component, and interconnections to route signals from one or more of the sensing components to a computing device is provided. An application causes the computing device to determine that an individual is at risk for developing a pressure ulcer. In response to determining that the individual is at risk for developing a pressure ulcer, the application can alert a manual intervention or trigger an automated intervention between the individual and the surface.

13 Claims, 7 Drawing Sheets

(51) Int. Cl.
*A61G 5/10* (2006.01)
*A61G 7/057* (2006.01)
*G16H 10/60* (2018.01)
*G16H 40/67* (2018.01)
*G16H 50/30* (2018.01)
*H04L 67/12* (2022.01)

(52) U.S. Cl.
CPC ............ *A61B 5/7275* (2013.01); *A61B 5/746* (2013.01); *A61F 5/01* (2013.01); *A61G 5/10* (2013.01); *A61G 7/057* (2013.01); *G16H 10/60* (2018.01); *G16H 40/67* (2018.01); *G16H 50/30* (2018.01); *A61B 2560/0252* (2013.01); *A61B 2562/0247* (2013.01); *A61B 2562/029* (2013.01); *H04L 67/12* (2013.01)

(58) Field of Classification Search
CPC .... A61B 2560/0252; A61B 2562/0247; A61B 2562/029; A61F 5/01; A61G 5/10; A61G 7/057; A61G 7/05784; A61G 2203/30; A61G 2203/34; G16H 10/60; G16H 40/67; G16H 50/30; H04L 67/12
See application file for complete search history.

(56) References Cited

U.S. PATENT DOCUMENTS

| | | | |
|---|---|---|---|
| 10,827,844 B2 | 11/2020 | McKnight et al. | |
| 10,874,330 B2 | 12/2020 | Larson et al. | |
| 2006/0264796 A1* | 11/2006 | Flick | A61F 13/022 602/48 |
| 2006/0293613 A1* | 12/2006 | Fatehi | A61B 5/447 600/595 |
| 2012/0065547 A1* | 3/2012 | Hann | A61B 5/11 600/587 |
| 2012/0116251 A1* | 5/2012 | Ben-Shalom | A61B 5/447 600/587 |
| 2012/0283979 A1* | 11/2012 | Bruekers | A61B 5/01 702/141 |
| 2016/0317370 A1* | 11/2016 | Evans | G05B 15/02 |
| 2017/0172490 A1* | 6/2017 | Afentakis | A61B 5/6892 |

* cited by examiner

PRESSURE ULCER PREVENTION SYSTEM

CROSS-REFERENCE TO RELATED APPLICATIONS

This application is the National Stage of International Application No. PCT/US2019/022650, filed Mar. 16, 2019, which claims priority to U.S. Provisional Patent Application No. 62/644,044, filed Mar. 16, 2018, which are entirely incorporated herein by reference.

TECHNICAL FIELD

The present disclosure generally relates to pressure ulcer prediction, alleviation and/or prevention systems including one or more sensors.

BACKGROUND

Pressure ulcers (pressure injuries) are high-cost adverse events across the spectrum of healthcare settings and populations including spinal cord injury (SCI) individuals and pediatric care. Conventional techniques for controlling pressure ulcers involve envelopment and immersion into cushions, offloading pressure, and turning or repositioning an individual on a periodic basis. These techniques can be costly and can negatively impact an individual's quality of life. Therefore, there is a need for systems and methods that can predict, alleviate or slow the formation and/or prevent pressure injuries.

SUMMARY

Disclosed herein are pressure ulcer prediction, alleviation and/or prevention systems and methods to address the aforementioned deficiencies. In various aspects, the present systems and methods can comprise one or more fabric-based sensors that can be placed between an individual and a wheelchair, seat, bed, crib, or other equipment or device upon which the individual can sit or lie or with which the individual is in contact. The fabric-based sensor(s) can comprise a combination of material types, fabric structures (single, multilayer, and their inherent variations), and manufacturing technologies (weaving, knitting and fabric finishing, and combinations thereof) and a combination of woven/knitted structures and sensors.

The present pressure ulcer prediction, alleviation and/or prevention systems and methods help predict, alleviate or slow, and/or prevent the formation of pressure ulcers in individuals—from newborn to the elderly. They can include a prediction/prevention application, an analytics application, and/or a caregiver application for implementation on various computing environments including a single-board computer or a server, smartphone, a tablet, laptop, or other computing device. The systems and methods can alert or trigger a manual intervention or an automated intervention regarding the individual and the individual's contact with the equipment.

In an embodiment, a system for predicting, alleviating or slowing, and/or preventing the formation of pressure ulcers is provided. The system can include a fabric-based sensing component (also referred to herein as a "fabric-based sensor"). The fabric-based sensor can include one or more sensors such as one or more pressure sensors or one or more moisture sensors or both. In some examples, the fabric-based sensor can include a pressure sensing component, or a moisture sensing component, or both. When both a pressure sensing component and a moisture sensing component are provided an insulator can be provided between the moisture sensing component and the pressure sensing component. The fabric-based sensor can be configured to be placed between an individual and a wheelchair, seat, bed, crib, or other equipment or device upon which the individual can sit or lie or with which the individual is in contact (such as a body brace, e.g., a neck brace, a knee brace, etc., or a body cast). In any one or more aspects, the pressure sensing component can include two high conductive fabrics configured to make contact through a low conductive fabric forming a pressure sensor. It can be configured to detect or measure a pressure at an interface location between the fabric-based sensor and the individual. In any one or more aspects, the moisture sensing component can include two conductive fabrics placed adjacent or next to each other forming a moisture sensor, the two conductive fabrics optionally separated by an insulating fabric, wherein moisture closes the circuit in the moisture sensor when moisture passes or percolates from one of the conductive fabrics to the other of the conductive fabrics. It can be configured to detect or measure moisture at an interface location between the fabric-based sensor and the individual. The fabric-based sensor can also include interconnections to route signals from the one or more pressure sensing components and the one or more moisture sensing components or both to a network or a computing device.

In any one or more aspects, the system(s) can include a computing device with a processor, a data store, and an application that, when executed, causes the computing device to determine that an individual is at risk for developing a pressure ulcer at an interface location between the individual and the equipment or device with which the individual is in contact through the fabric-based sensor that can include a pressure sensing and/or a moisture sensing component. As used herein "an interface location" means a point of contact between the individual or a part of the body of the individual and the equipment or device, or a surface of the equipment or device, with which the individual is in contact through the fabric-based sensor, it being understood that the fabric-based sensor would be placed or positioned between the individual and the equipment or device to obtain the various measurements described herein.

The application can obtain, from the fabric-based sensor, at least one measurement corresponding to a pressure and/or a moisture associated with at least one point of contact through the fabric-based sensor between the individual and an interface location. The system(s) can also obtain a reading of an environmental condition such as a temperature or a relative humidity in relation to or at or about the interface location.

Determining that the individual is at risk for developing a pressure ulcer can include the application determining that the pressure and/or the moisture exceeds a threshold value, for example at an interface location. In response to determining that the individual is at risk for developing a pressure ulcer, the application can alert or trigger a manual intervention or an automated intervention or both regarding the individual and one or more points of contact, or interface locations, between the individual and the equipment or device. The systems can also include an analytics system configured to apply one or more machine learning techniques to create a knowledge base for anticipating and predicting, alleviating or slowing, and/or preventing formation of pressure ulcers.

Methods of predicting, alleviating or slowing, and/or preventing pressure ulcers are also provided. The methods can include obtaining, from a fabric-based sensing component ("fabric-based sensor"), one or more measurements corresponding to a pressure or a moisture associated with at least one point of contact at an interface location between the individual and the equipment or device through the fabric-based sensor that can include a pressure sensing and/or a moisture sensing component. The methods can also include determining that the individual is at risk for developing a pressure ulcer at an interface location based at least in part on one or more pressure and/or moisture measurements. In response to determining that the individual is at risk for developing a pressure ulcer, the method(s) can alert or trigger a manual intervention or an automated intervention between the individual and the equipment or device with which the individual is in contact, in particular at the interface location. Determining that the individual is at risk for developing a pressure ulcer can include determining that at least one of the measurements exceeds a threshold value. In any one or more aspects, determining that the individual is at risk for developing a pressure ulcer can include determining that a composite assessment of a pressure and a moisture exceeds a threshold value.

A pressure ulcer system can include a fabric-based sensing component ("fabric-based sensor") and a computing device. The fabric-based sensor can include one or more sensors comprising a pressure sensor or a moisture sensor or both. The computing device can include a processor and an application that can include program instructions stored in memory and executable by the processor that, when executed, can cause the computing device to determine that an individual is at risk for developing a pressure ulcer at an interface location between the individual and a surface of a piece of equipment or device with which the individual is in contact through the fabric-based sensor, and in response to determining that the individual is at risk for developing the pressure ulcer at the interface location, alert a manual intervention or trigger an automated intervention or both. The surface can be a surface of any of the aforementioned equipment or devices, such as a chair, crib, bed, wheel chair, or other equipment or a device (such as a body brace or cast), and the fabric-based sensor can be between the individual and the surface.

The program instructions can cause the computing device to obtain, from the fabric-based sensor, at least one measurement corresponding to at least one of: a pressure or a moisture value associated with at least one contact point between the individual and the equipment or device at an interface location. The program instructions can also cause the computing device to process the at least one measurement of the pressure or the moisture value. Determining that the individual is at risk for developing a pressure ulcer can comprise determining that the at least one measurement exceeds a designated threshold value. The program instructions can cause the computing device to obtain a reading of an environmental condition in relation to or at or about the interface location.

The pressure ulcer system can include a data store. The program instructions can cause the computing device to store the at least one measurement in the data store. The pressure ulcer system can include an analytics system configured to apply machine learning techniques to the at least one measurement to create a knowledge base for anticipating, avoiding and/or preventing formation of pressure ulcers.

Methods for predicting, alleviating or slowing, and/or preventing pressure ulcers are also provided, wherein the methods include obtaining, from a fabric-based sensing component ("fabric-based sensor"), one or more measurements corresponding to at least one of: a pressure and a moisture value associated with at least one contact point of an individual at an interface location between the individual and a surface with which the individual is in contact as described elsewhere herein. The surface can be a surface of a chair, crib, bed, wheelchair, or other equipment or a device (such as a body brace or cast), and the fabric-based sensor can be placed between the individual and the surface. The fabric-based sensor can include a pressure sensing component configured to detect or measure the pressure or a moisture sensing component configured to detect or measure the moisture or both at the interface location.

The method(s) can include determining that the individual is at risk for developing a pressure ulcer at the interface location based at least in part on the one or more measurements, and in response to determining that the individual is at risk for developing the pressure ulcer, alerting a manual intervention or triggering an automated intervention or both. The fabric-based sensor can include a plurality of pressure sensors or moisture sensors or both.

In any one or more embodiments and aspects herein, the method(s) can include processing the one or more measurements. Determining that the individual is at risk for developing the pressure ulcer can include determining that at least one of the plurality of measurements exceeds a designated threshold value. Determining that the individual is at risk for developing a pressure ulcer can also include determining that a composite assessment of the pressure and the moisture value exceeds a designated threshold value or values. The methods can include obtaining a reading of an environmental condition in relation to or at or about the interface location.

A fabric-based sensing component ("fabric-based sensor") is provided that can include a pressure sensing component, or a moisture sensing component, or both and optionally an insulator between the moisture sensing component and the pressure sensing component. The pressure sensing component can be configured to detect a pressure at an interface location between an individual and a surface (such as described herein) with which the individual is in contact through the fabric-based sensor. The pressure sensing component can include two high conductive fabrics configured to make contact through a low conductive fabric. The moisture sensing component can be configured to detect a moisture at an interface location between an individual and a surface (such as described herein) with which the individual is in contact through the fabric-based sensor. The moisture sensing component can include two conductive fabrics placed next to or adjacent each other such that when moisture passes from one of the conductive fabrics to the other of the conductive fabrics, the moisture closes a circuit between the fabrics. Optionally, a substrate or insulating fabric can be provided between the two conductive fabrics through which the moisture can pass from the one conductive fabric to the other conductive fabric to form the moisture sensing component. The pressure sensing component can include an array of pressure sensors and the moisture sensing component can include an array of moisture sensors configured to obtain pressure and moisture readings at multiple interface locations between the individual and the surface of the equipment or device. The fabric-based sensor can also include interconnections to route signals from the pressure sensing component and the moisture sensing component to a computing device. In various aspects herein, the fabric-based sensor can include both a pressure sensing component and a moisture sensing component (such as described in any one or more aspects herein), one of the sensing components formed as a layer on top of the other sensing component, optionally with an insulating layer placed in between the two sensing component layers.

In an embodiment, a pressure ulcer system is provided, comprising: a fabric-based sensing component; and a computing device comprising: a processor; and an application comprising program instructions stored in memory and executable by the processor that, when executed, cause the computing device to: determine that an individual is at risk for developing a pressure ulcer at an interface location between the individual and a surface with which the individual is in contact through the fabric-based sensing component; and in response to determining that the individual is at risk for developing a pressure ulcer at the interface location, alert a manual intervention or trigger an automated intervention between the individual and the surface.

In any one or more aspects of the system, the program instructions can cause the computing device to obtain, from the fabric-based sensing component, at least one measurement corresponding to at least one of: a pressure or a moisture value associated with at least one contact point between the individual and the surface through the fabric-based sensing component at the interface location. The program instructions can cause the computing device to process the at least one measurement of the pressure or the moisture value. Determining that the individual is at risk for developing the pressure ulcer can comprise determining that the at least one measurement exceeds a designated threshold value. The system can comprise a data store and the program instructions can cause the computing device to store the at least one measurement in the data store. The system can further comprise an analytics system configured to apply machine learning techniques to the at least one measurement to create a knowledge base for anticipating and avoiding formation of pressure ulcers. The program instructions can cause the computing device to obtain a reading of an environmental condition. The alert for a manual intervention can require a caregiver for the individual to acknowledge the alert by entering a response into the system. The at least one measurement can be transmitted to a data store for storing electronic medical records. The fabric-based sensing component can comprise a pressure sensing component or a moisture sensing component or both.

In an embodiment, a method for alleviating pressure ulcers is provided, comprising: obtaining, from a fabric-based sensing component, one or more measurements corresponding to at least one of: a pressure or a moisture value associated with at least one contact point of an individual at an interface location between the individual and a surface with which the individual is in contact through the fabric-based sensing component; determining that the individual is at risk for developing a pressure ulcer at the interface location based at least in part on the plurality of measurements; and in response to determining that the individual is at risk for developing the pressure ulcer, alerting a manual intervention or triggering an automated intervention between the individual and the surface.

In any one or more aspects, the method can comprise: processing the one or more measurements; and wherein determining that the individual is at risk for developing a pressure ulcer can comprise determining that at least one of the one or more measurements exceeds a designated threshold value. Determining that the individual is at risk for developing a pressure ulcer can comprise determining that a composite assessment of the pressure and the moisture value exceeds a designated threshold value or values. The method can comprise obtaining a reading of an environmental condition. The fabric-based sensing component can comprise a pressure sensing component configured to detect a pressure, or a moisture sensing component configured to detect the moisture, or both, at the interface location. The method can further comprise: receiving a picture of the interface location; and rendering a user interface to allow a wound specialist to view the picture. The alert for a manual intervention can comprise requiring a caregiver for the individual to acknowledge the alert by entering a response into a system. The one or more measurements can be transmitted to a data store for storing electronic medical records.

In an embodiment, a fabric-based sensing component is provided, comprising: a pressure sensing component; a moisture sensing component; and an insulator between the moisture sensing component and the pressure sensing component. In any one or more aspects, the pressure sensing component is configured to detect a pressure at an interface location between an individual and a surface with which the individual is in contact through the fabric-based sensing component. The moisture sensing component is configured to detect a moisture at an interface location between an individual and a surface with which the individual is in contact through the fabric-based sensing component. The pressure sensing component can comprise two high conductive fabrics configured to make electrical contact through a low conductive fabric. The moisture sensing component can comprise two conductive fabrics configured to make contact through moisture between the two conductive fabrics. The fabric-based sensing component can comprise interconnections to route signals from the pressure sensing component and the moisture sensing component to a computing device.

In any one or more aspects of any one or more embodiments herein the fabric-based sensing component can comprise a plurality of sensors comprising at least a pressure sensor or a moisture sensor. The pressure sensing component can comprise a plurality of pressure sensors for detecting or measuring a pressure at a plurality of interface locations. The moisture sensing component can comprise a plurality of moisture sensors for detecting or measuring a moisture at a plurality of interface locations. The plurality of pressure sensors can be located or positioned in an array to cover an area or the entire body of the individual. The plurality of moisture sensors can be located or positioned in an array to cover an area or the entire body of the individual. The array of pressure sensors and/or the array of moisture sensors can be configured to obtain pressure and/or moisture readings at multiple interface locations between the individual and the surface. The surface can be a surface of a chair, crib, bed, wheelchair, or other equipment or device for supporting a body or a body part of the individual, and the fabric-based sensing component can be placed between the individual and the surface.

Other systems, methods, features, and advantages of the present disclosure for a pressure ulcer system, will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
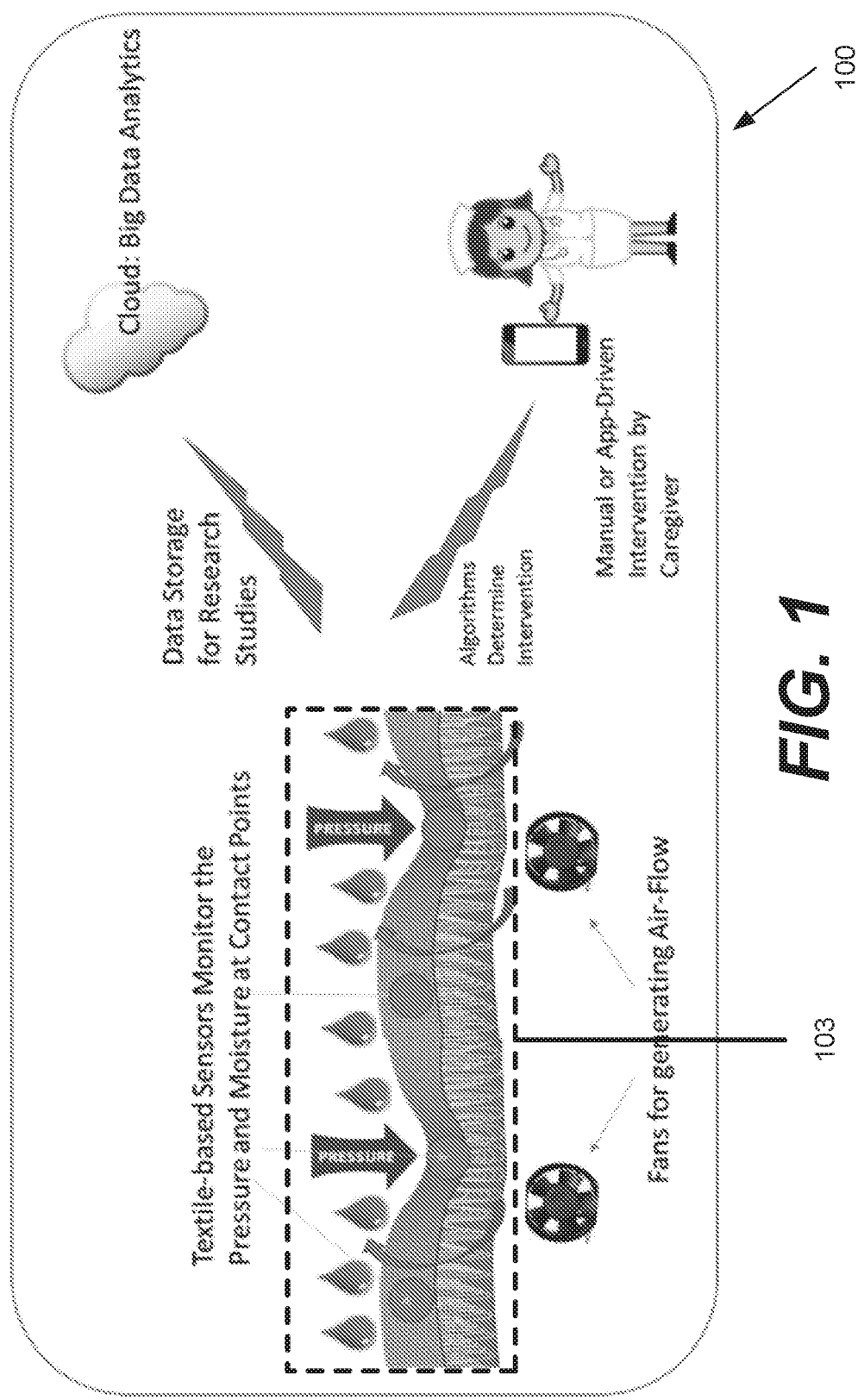
FIG. 1 depicts one example of a prevention system having a unit cell of a fabric-based sensor of a fabric-based sensor network of the present disclosure.

Described below are various embodiments of a pressure ulcer prevention system. Although particular embodiments are described, those embodiments are mere exemplary implementations of the system, method, and non-transitory computer-readable medium. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for.

It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

A motivation for this disclosure is that "Investment in the prevention of pressure ulcers is much less than the cost of treatment." In fact, the cost of treating pressure ulcers has been estimated to be 2.5 times the cost of preventing them. Thus, pressure ulcers are high-cost adverse events across the spectrum of healthcare settings and populations including pediatric care. Pressure ulcer prevalence rates have been reported to be as high as 27% in pediatric intensive care units and as high as 23% in neonatal intensive care units. Among noncritical hospitalized pediatric patients, prevalence rates of 0.47% to 13%, and incidence rates of 0.29% to 6% have been reported. Pressure ulcers lead to wounds and infection and thereby negatively impact the recovery of the patient from the primary illness or injury necessitating the admission. Thus, there is a critical need for a cost-effective intervention that can address the significant issue of pressure ulcers—a "Never Event" or Hospital-acquired Infection—and enhance the quality of care for individuals and patients while reducing healthcare costs, which currently account for about 17.8% of GDP in our Nation.

While the present disclosure references a pressure ulcer system that can detect, ameliorate, slow the progression and/or prevent the formation of pressure ulcers in individuals (sometimes referred to as a "pressure ulcer prevention system" for short), it should be appreciated that the present systems and methods can be used by office workers, drivers, and any other individuals in contact with a piece of equipment or device (e.g., the individual is sitting on a chair for a prolonged period of time). The systems and methods herein can detect and give relief to lower back pain and/or other discomfort associated with contact between the individual and a piece of equipment or device (such as described herein).

In any one or more embodiments, provided herein are pressure ulcer prevention systems, methods and components to address the aforementioned deficiencies. In any one or more aspects, the systems include a fabric-based sensing component ("fabric-based sensor") configured to be placed between an individual and a wheelchair, seat, crib, or other equipment or device upon which the individual can sit or lie or with which the individual is in contact. The fabric-based sensor can include a combination of material types, fabric structures (single, multilayer, and their inherent variations), and manufacturing technologies (weaving, knitting and fabric finishing, and combinations thereof) and a combination of woven/knitted structures.

The pressure ulcer prevention systems, methods and components can help detect, ameliorate, slow the progression, and/or prevent the formation of pressure ulcers in individuals—from newborn to the elderly. They can include a prediction/prevention application (sometimes referred to herein as a "prevention application" or simply as "an application"), an analytics application, and a caregiver application for implementation on various computing environments including a single-board computer or a server, smartphone, a tablet, laptop, or other computing device. They can trigger a manual intervention or an automated intervention regarding the individual and the individual's position on the equipment.

In any one or more aspects, a system for predicting, alleviating or slowing and/or preventing pressure ulcers is provided. The system can include a fabric-based sensing component ("fabric-based sensor"). The fabric-based sensor can include one or more sensors such as one or more pressure sensors and/or one or more moisture sensors. In some aspects, the fabric-based sensor includes a pressure sensing component. In some aspects, the fabric-based sensor includes a moisture sensing component. In some aspects, the fabric-based sensor includes a pressure sensing component, a moisture sensing component, and an insulator between the moisture sensing component and the pressure sensing component. The fabric-based sensor can be configured to be placed between an individual and a wheelchair, seat, crib, or other equipment or device (such as a body brace or cast) upon which the individual can sit or lie or with which the individual is in contact. In any one or more aspects thereof, the pressure sensing component can include two high conductive fabrics configured to make contact through a low conductive fabric. As used herein "fabric" can mean or include pieces of fabric, such as fabric patches. The pressure sensing component can be configured to detect a pressure at an interface location. The moisture sensing component includes two conductive fabrics configured to make contact through the flow or percolation of moisture therebetween. It is configured to detect moisture at an interface location. For either or both sensing component the interface location can be a location, and/or point of contact between the individual and a piece of equipment or device (such as described herein) through the fabric-based sensing component. The fabric-based sensor can also include interconnections to route signals from the pressure sensing component, the moisture sensing component, or both, to a computing device.

The system(s) can also include a computing device with a processor, a data store, and an application that, when executed, causes the computing device to determine that an individual is at risk for developing a pressure ulcer at the interface location. The application can obtain, from the fabric-based sensor, at least one measurement corresponding to a pressure, a moisture, or both, associated with at least one contact point at the interface location between the individual and the piece of equipment or device through the sensing component. The system(s) can also obtain a reading of an environmental condition such as temperature or relative humidity in a local area at or about the point of contact or interface location between a wheelchair, seat, bed, crib, or other equipment or device (such as a body brace or cast).

Determining that the individual is at risk for developing a pressure ulcer can include the application determining that the pressure or the moisture measured or sensed by the sensing component exceeds a threshold. The threshold can be, for example, a particular pressure or a particular moisture level or value, and/or a particular period of time or time duration during which the pressure and/or moisture threshold is exceeded.

In response to determining that the individual is at risk for developing a pressure ulcer, the application can alert or trigger a manual intervention or an automated intervention. The system can also include an analytics system configured to apply machine learning techniques to create a knowledge base for anticipating and avoiding formation of pressure ulcers based on the measured or sensed pressure(s) and moisture(s).

Methods of preventing pressure ulcers are also provided. The methods can include obtaining, from a fabric-based sensor, one or more measurements corresponding to a pressure or a moisture or both, associated with at least one contact point of an individual at an interface location between the individual and a piece of equipment or device (such as described herein) through the fabric-based sensor. The methods can also include determining that the individual is at risk for developing a pressure ulcer at the interface location based at least in part on the one or more measurements. In response to determining that the individual is at risk for developing a pressure ulcer, the method(s) can alert or trigger a manual intervention or an automated intervention or both. Determining that the individual is at risk for developing a pressure ulcer can include determining that at least one of the measurements exceeds a threshold or threshold value such as that described above. In any one or more aspects herein, determining that the individual is at risk for developing a pressure ulcer can include determining that a composite assessment of the pressure and the moisture measurements or measured values exceeds a threshold or threshold value such as that described above.

As will be apparent to those of skill in the art upon reading this disclosure, each of the individual embodiments described and illustrated herein has discrete components and features which may be readily separated from or combined with the features of any of the other several embodiments and aspects without departing from the scope or spirit of the present disclosure. Any recited method can be carried out in the order of events recited or in any other order logically possible.

FIG. 1 depicts one example of a system 100 of the present disclosure. The system 100 has a unit cell 103 of a fabric-based sensor of a fabric-based sensor network. The system 100 is a textile-based Pressure Ulcer Prevention System (PUPS) that is designed to predict, detect, alleviate or slow and/or prevent the occurrence of pressure ulcers for individuals—from newborns to the elderly—who may be at risk for development of a pressure injury due, e.g., to lying or sitting for a prolonged period of time on a surface such as a bed, chair, crib or other equipment on which the individual may lie or sit, or for a prolonged period of time of contact with a surface of a device such as a brace or cast.

The unit cell 103 can have one or more sensors 105, 107 (see, e.g., FIG. 2) to monitor the parameters of pressure and/or wetness (moisture) at the contact surface points between an individual and the surface. The one or more pressure sensors 105 can be positioned in contact with or can comprise a low conductive fabric sandwiched in between high conductive fabric to form a pressure sensing component. The one or more moisture sensors 107 can be formed of two or more layers of conductive fabric positioned to make contact through the flow of moisture therebetween. The two or more layers can for example be positioned with a top and bottom layer (see, e.g., FIG. 2). When both a pressure sensing component and a moisture sensing component are provided together in the system 100 a moisture insulating layer or barrier can be placed between the pressure sensing and moisture sensing components to prevent moisture from passing through the barrier from the moisture sensing component to the pressure sensing component.

Sensor(s) 105, 107 can be monitored and measured periodically to determine a duration and/or a degree of pressure, amount and/or duration of moisture, etc. The system 100 can process the data using algorithms based on the duration and degree of pressure and/or moisture, and determine an appropriate intervention, which can be effected manually through an alert to the individual (or caregiver) or through actuators and/or a ventilation system built on into the underlying surface, such as shown in FIG. 1. The data can also be stored to create large data sets on which analytics can be performed to develop better interventions and/or serve as a research database for pressure ulcers in different populations. The intervention can be in the form of moving or causing the individual to move or roll over to relieve the pressure and/or reduce the moisture at the measured or determined interface or point of contact or otherwise transfer pressure from one point of contact to another point of contact.

In some examples, the system 100 can trigger one or more automated interventions when specific thresholds of pressure, duration, environmental data, and/or calculated composite measurements are reached. Automated interventions can include activating actuators within or associated with the equipment or device to effect a controlled movement of an individual, vibrate a contact point, etc. Likewise, an automated intervention can include causing a fan or other air circulation system to provide ventilation to and reduce moisture at the contact point. The system 100 can trigger an intervention based on a particular sensor of a fabric-based sensor, or based on an aggregate of measurements of sensors to identify a body part affected. The system 100 can provide features of manual interventions for alerting caregivers in healthcare settings to intervene, e.g., move the patient or a specific part of the body of the patient or individual.

The system 100 can also serve as a data acquisition platform to facilitate Big Data analytics and the resulting insights should be valuable to clinicians and designers of equipment, such as wheelchairs, cribs, and beds. For example, patients are typically "turned around" every two hours to avoid the formation of pressure ulcers. System 100 can provide real-time data that, over time, can lead to "evidence-based" decision-making thereby enhancing the quality of care for the SCI individual. In a non-hospital setting, the SCI individual can suitably alter the seating/usage pattern to avoid the formation of pressure ulcers. Thus the system 100 can significantly enhance the quality of care for patients in long-term care in hospitals while reducing healthcare costs.

The roles of pressure and moisture or wetness at one or more points of contact between an individual and a surface, such as an underlying surface (a bed, chair, seat or crib) or an adjacent surface (for example, a surface of a brace or cast) in causing discomfort to individuals and the conditions for the onset of pressure ulcers can be investigated in consultation with dermatologists, hospital intensivists, and expert physicians treating SCI individuals. Transmission of the one or more measurements of pressure and/or moisture and/or processed signals of the one or more measurements can be over a wired connection, such as a network, to a laptop and subsequently migrated to wireless transmission through Bluetooth® or Zigbee® protocols to a remote device (e.g., a smartphone, a tablet, or a laptop). The developed algorithms can be implemented on the individual or caregiver's device (e.g., a smartphone, a tablet, or a laptop), which can present an intervention "alert" to the SCI individual or caregiver. In an automatic intervention mode, it can trigger the actuators and ventilation system to change the ambient conditions at the surface contact points.

A factor in predicting, alleviating, slowing, and/or preventing the formation of pressure ulcers is to change the conditions at the contact points between the body and the underlying surface (wheelchair, seat, crib, bed, brace or cast) before a threshold (such as a pressure and/or moisture threshold) is reached. The system 100 can for example relieve and change pressure distribution by physically changing the contact points by actuating the components as in a piano keyboard. The system 100 can also change the localized atmospheric conditions at the surface contact points, and hence the moisture or wetness levels, by circulating air through a built-in ventilation system.

Figure 2:
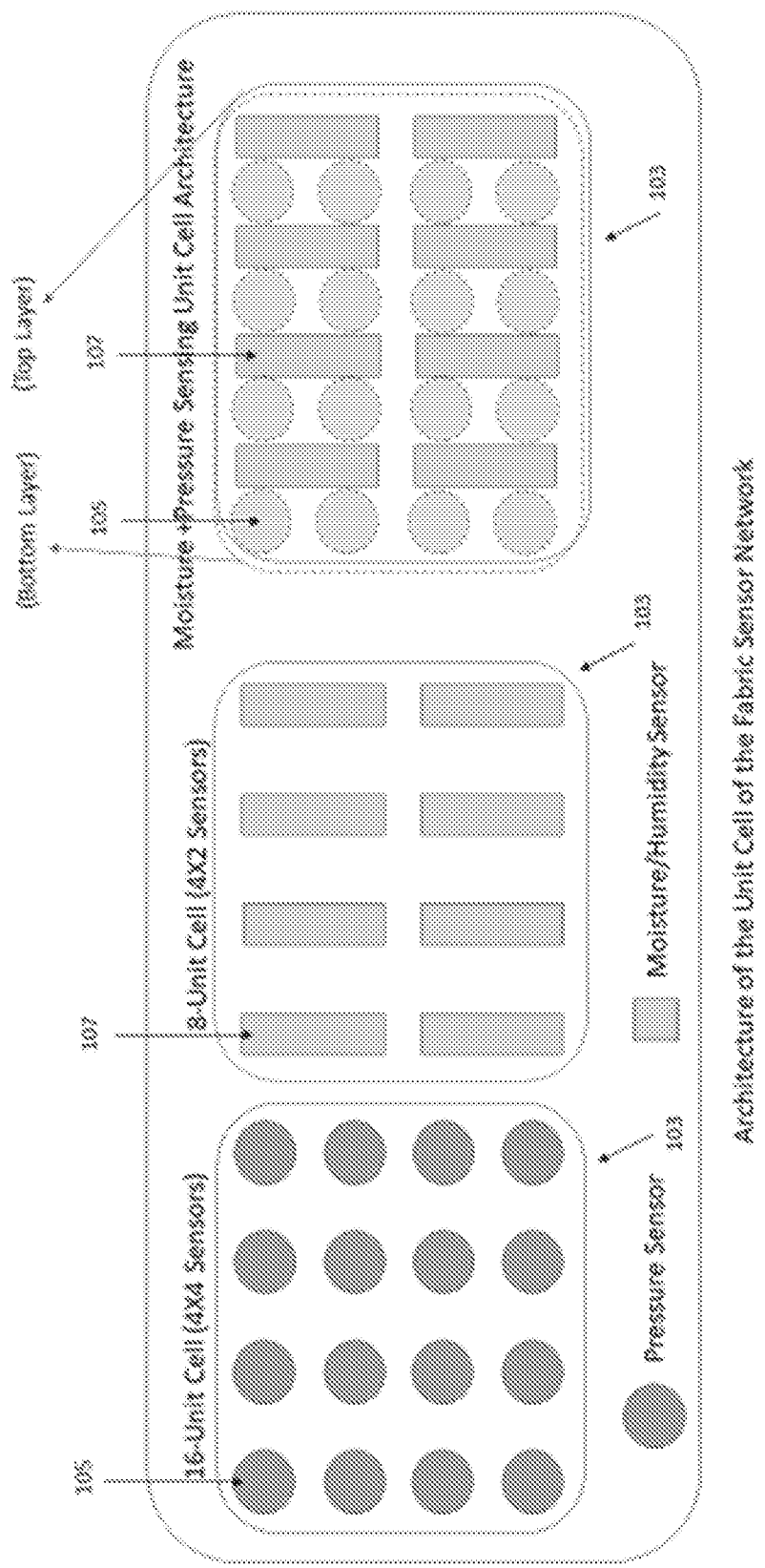
FIG. 2 is an exemplary architecture of a unit cell of a fabric-based sensor of a fabric-based sensor network of the present disclosure.

FIG. 2 is an example architecture of a unit cell 103 of a sensing component of a fabric-based sensor network. Each moisture and pressure sensing unit cell 103 can have, for example, an array of 16 pressure and 8 moisture sensors distributed over a nominal 6"×6" surface area, which can be changed to meet specifications or as preferred. This density of sensors can give the desired sensitivity or resolution of the parameters for accurate monitoring of pressure and/or moisture at the surface contact points over different areas. The elegance of the proposed sensor architecture and its realization in a textile fabric lies in the ability to configure and customize the resolution to suit the desired monitoring location. For instance, the number of sensors for monitoring the ischial tuberosities will be different from that needed at the lateral malleolus. A unit cell 103 can easily be combined with other unit cells 103 to create sensing component comprising the sensors 105, 107 and fabric-based sensor of a needed dimension, for example 12"×12" or 18"×18". In developing a unit cell 103, processing capabilities (I/O pins) of the hardware have been taken into consideration so that the unit cell 103 can be scaled up or down to meet the desired application.

As depicted in FIG. 2, a unit cell 103 can include one or more pressure sensors 105 positioned in contact with or can comprise a low conductive fabric sandwiched in between high conductive fabric to form a pressure sensing component. The unit cell 103 can also include one or more moisture sensors 107 positioned to make contact through the flow of moisture therebetween. The unit cell 103 as depicted can include a top layer and a bottom layer. In some aspects, one or more pressure sensors 105 can be disposed in the bottom layer and one or more moisture sensors 107 can be disposed in the top layer. Example applications, as will be discussed further with respect to FIG. 3, can include a fabric sensing component that can be used by an individual in a wheelchair, or other chair or seat, bed, or crib, or a brace or cast. The fabric sensing component can monitor the parameters of pressure and/or wetness at the contact surface points of individuals, e.g., spinal cord injury (SCI) individuals in wheelchairs and in beds or individuals having to wear a brace or a cast for a prolonged period of time.

Figure 3:
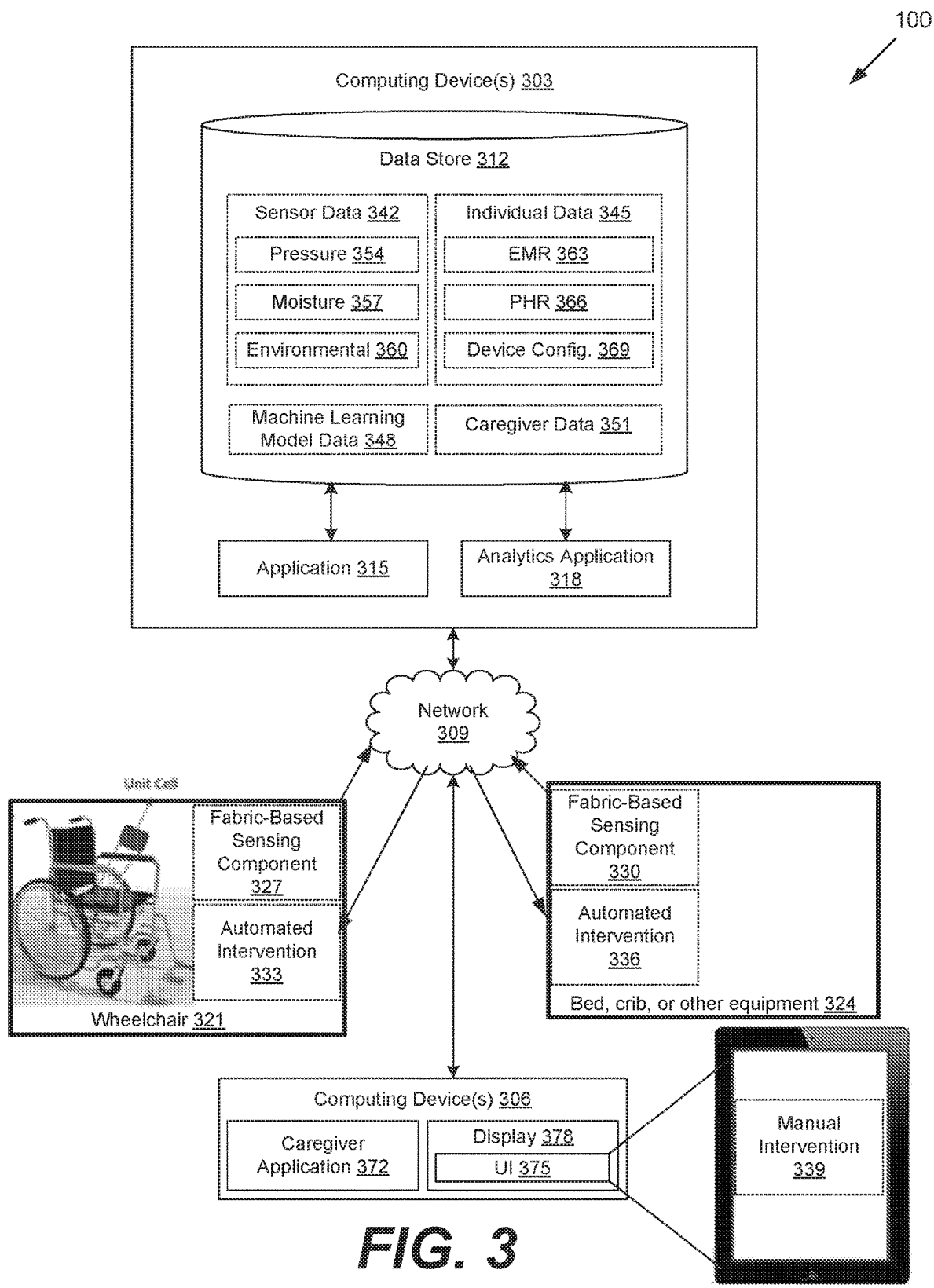
FIG. 3 is a schematic block diagram of a prevention system according to various embodiments of the present disclosure.

With reference to FIG. 3, shown is a schematic block diagram of a system 100 that provides monitoring, analysis, and notification for enhancing the quality of life of individuals susceptible to pressure ulcers. The system 100 includes at least one computing device 303 and one or more computing devices 306, which are in data communication with each other via a network 309. The network 309 includes, for example, the internet, intranets, extranets, wide area networks (WANs), local area networks (LANs), wired networks, wireless networks, cable networks, satellite networks, or other suitable networks, etc., or any combination of two or more such networks.

The computing device 303 can comprise, for example, a server computer or any other system providing computing capability. Alternatively, the computing device 303 can employ a plurality of computing devices that can be arranged, for example, in one or more server banks, computer banks, or other arrangements. Such computing devices can be located in a single installation or can be distributed among many different geographical locations. For example, the computing device 303 can include a plurality of computing devices that together can comprise a hosted computing resource, a grid computing resource, and/or any other distributed computing arrangement. In some cases, the computing device 303 can correspond to an elastic computing resource where the allotted capacity of processing, network, storage, or other computing-related resources can vary over time.

Various applications and/or other functionality can be executed in the computing device 303 according to various embodiments. Also, various data is stored in a data store 312 that is accessible to the computing device 303. The data store 312 can be representative of a plurality of data stores 312 as can be appreciated. The data stored in the data store 312, for example, is associated with the operation of the various applications and/or functional entities described below.

The components executed on the computing device 303, for example, include an application 315, an analytics application 318, and other applications, services, processes, systems, engines, or functionality not discussed in detail herein. The application 315 is executed in order to predict, alleviate or slow and/or prevent the formation of a pressure ulcer (also known as pressure injury) at an interface or point of contact between an individual and a surface, such as an underlying surface in the case of a wheelchair 321 or bed, crib, or other equipment 324 or an adjacent surface of a device such as in the case of a brace or cast. Equipment 324 is not limited to beds and cribs, and can include automobile seats, office chairs, neck braces, respiratory equipment, or any other equipment where an individual is in contact with a surface of the equipment or device and the individual is at risk for the formation of a pressure injury at an interface or point of contact between the individual and the other equipment 324.

The application 315 can perform various functions associated with the prediction, alleviation or slowing and/or prevention of pressure injuries as will be described. To this end, the application 315 can trigger automated intervention 333, automated intervention 336, or manual intervention 339 as described in any aspect herein.

The application 315 can trigger automated interventions 333, 336 in a number of ways. Actuators can be triggered for example to vibrate segments of the surface of the equipment, such as an individual's seat on the wheelchair 321. In some examples, actuators can actively control portions of the wheelchair 321 or the equipment 324. Actuators can raise or lower slats in the wheelchair 321, or position the equipment 324 to relieve pressure, or cause the individual to change position to relieve the pressure at a given determined contact point. Based on a pressure at a contact point with the wheelchair 321, the application 315 can determine that a particular slat of the wheelchair 321 needs to be lowered (or raised) and cause an actuator to lower (or raise) the particular slat. Or, the application 315 can cause a head of bed elevation (HOBE) of the bed 324 to be adjusted. The application 315 can also turn on one or more fans to ventilate one or more contact surface points associated with the wheelchair 321 or the equipment 324 to relieve moisture or wetness at such points. The application 315 can also generate network pages such as web pages or other types of network content that are provided to computing device 306 for the purposes of viewing pressure and moisture levels along with environmental conditions as will be described.

The manual intervention 339 can be a web page that is rendered to alert a caregiver or an individual to take some manual action, such as to flip or reposition the individual. One particular advantage of the system 100 is that the manual intervention 339 can be alerted or triggered as needed, rather than requiring manual interventions on a set periodic schedule (e.g., every 15 minutes or two hours in some protocols). For example, the application 315 can refrain from triggering a manual intervention 339 if a child in a crib 324 has recently been picked up and thus the risk of developing a pressure injury is lower. The application 315 can determine that a threshold has not been reached, and thus a caregiver does not need to come to reposition the child.

The application 315 is configured to monitor and receive readings or signals from the sensors 105, 107 representative of a pressure or a moisture level of a fabric-based sensor 327 associated with the wheelchair 321 and/or sensors of a fabric-based sensing component 330 associated with the equipment 324. The fabric-based sensing component 327, 330 can have multiple layers, for example one or more layers that make up a pressure sensing component or one or more layers that make up a moisture sensing component or both. One or more layers can be made up of a number of unit cells 103 (as depicted in FIGS. 1 & 2). Additionally, the fabric-based sensing component 327, 330 can include an insulator or an insulating layer between a moisture sensing component and a pressure sensing component. While the present disclosure focuses on the sensors 105, 107 for obtaining one or more measurements representative of the pressure or the moisture level of a fabric-based sensing component 327, 330, it should be appreciated that any type of sensor may be used to monitor parameters at the contact surface points between an individual and the underlying surface. The system 100 can include a sensor to measure surface friction and/or surface shear, which is another parameter that can affect the formation of pressure injuries.

In some examples, the fabric-based sensing component 327, 330 includes a pressure sensing component, a moisture sensing component, and an insulator between the moisture sensing component and the pressure sensing component. The fabric-based sensor 327, 337 is configured to be placed between an individual and the wheelchair 321 or other equipment 324 as described herein. The pressure sensing component of the fabric-based sensing component 327, 337 can include two high conductive fabrics configured to make contact through a low conductive fabric and is configured to detect a pressure at an interface location, as described in any one or more aspects herein. The moisture sensing component of the fabric-based sensing component 327, 337 can include two conductive fabrics configured to make contact through moisture and configured to detect and measure moisture at an interface location, as described in any one or more aspects herein. In any one or more aspects herein, high conductive can refer to a surface resistivity of between about 0.002 and about 8 ohms per square, and low conductive can refer to a surface resistivity of between about 10E3 and 10E13 ohms per square. The surface resistivity can also be a resistivity of one or more of a silver coated nylon thread, a metal clad nylon or aramid yarn, a carbon-based sheath, a conductive ink, and/or plastic such as Polyethylene (PE)/ Polypropylene (PP)/Polyethylene terephthalate (PET). The fabric-based sensing component 327, 337 can also include interconnections to route signals representative of a pressure and/or moisture level from the pressure sensing component or the moisture sensing component or both to the computing device 303 or the computing device 306.

In any one or more aspects herein, the interface location refers to at least one contact point of the individual and the wheelchair 321 or the other equipment 324 or device through the fabric-based sensing component. As described, the fabric-based sensing component 327, 330 can be placed between the individual and the wheelchair 321 or the other equipment 324 or device. The system 100 can obtain, from the fabric-based sensing component 327, 330, at least one measurement corresponding to a pressure 354 and/or a moisture 357 associated with the at least one contact point between the individual and the associated surface, such as the wheelchair 321 or the other equipment 324 or device. As the fabric-based sensing component 327, 330 can be between the individual and the wheelchair 321 or the other equipment 324, contact can be through the fabric-based sensing component 327, 330. The fabric-based sensing component 327, 330 can be in contact with a body or a portion of a body of the individual and/or the underlying surface such as the wheelchair 321 or the bed, crib, or other equipment 324 or device.

The fabric-based sensing component 327, 330 can include one or more unit cells 103 with sensors 105, 107 and data buses that have been integrated using weaving, knitting, embroidery, sewing/stitching, printing or other manufacturing techniques. Proposed manufacturing technologies and design parameters are also discussed with regard to FIG. 7. The performance of these techniques can determine a preferred method for the production of the fabric-based sensing component 327, 330. Interconnections route the signals from sensors 105, 107 to the network 309. The fabric-based sensing component 327, 330 can be soft, comfortable, shape-conformable, and produced so that it does not impede the mobility or position of the individual due to its presence at the interface of the body and the surface (wheelchair or bed, etc., respectively).

The fabric-based sensing component 327, 330 can be made from any textile fabric, like knitted fabric, woven fabric, and metamaterial such as thin foil or film. A fabric-based distributed sensor network is provided that is unobtrusive, shape-conforming, breathable, comfortable, and customizable. The fabric-based sensing component 327, 330 can be a part of a bedsheet on equipment 324, or a seat (or seat cushion) on wheelchair 321 or device and like any other natural article used by an individual. Moreover, one or more sensor densities in the fabric-based sensing component 327, 330 can be varied to suit the degree of desired resolution in each location on the body thus providing an additional degree of flexibility in customizing the solution.

The modularity built into the design of the system 100 allows deployment of the fabric-based sensing component 327, 330 to selective pressure points (e.g., only on the back of the head and heels) and yet enable the seamless integration of the data from all the desired locations. This flexibility is helpful for the clinician to target specific body locations that are more likely to be susceptible to pressure ulcers. Likewise, it can help the SCI individual focus on specific vulnerable areas depending on the nature and level of activity when using the wheelchair 321 or other equipment.

Sensors 105, 107 of the fabric-based sensor network can be distributed according to the application, such as wheelchair 321 or other equipment 324. In the example of fabric-based sensing component 327, it might be preferred to use a different material in between the sensors so that it can stretch between slats of the wheelchair 321. More sensors can be distributed towards the back, where pressure injuries tend to occur, with fewer sensors distributed towards the front. For the fabric-based sensor 330, it might be preferable to evenly distribute sensors along the surface of the bed or crib 324. The fabric-based sensor network can include one or more sensors 105, 107 connected for example by a conductive textile fiber yarn (e.g., metal-clad nylon or aramid, or stainless steel). The one or more sensors 105, 107 can be connected to form a data bus within the fabric-based sensing component 327, 330. The data bus can accommodate various bus widths and simplify (or reduce) the number of conductive fiber connections between the fabric-based sensing component 327, 330 and the application 315. For example a row of twelve sensors 105, 107 can be merged into a single data bus so the application 315 can use a single conductive fiber connection to receive one or more signals sent by the sensors 105, 107.

The data stored in the data store 312 includes, for example, sensor data 342, individual data 345, machine learning model data 348, caregiver data 351, and potentially other data. The sensor data 342 includes information aggregated from a plurality of sensors in the fabric-based distributed sensor network of the system 100, including pressure 354 and/or moisture 357. The sensor data 342 can also include environmental data 360.

The system 100 can integrate the effects of parameters that can cause pressure ulcers, for example: pressure 354 and moisture 357 at the interface of the individual and the surface the wheelchair 321 or the other equipment 324. Environmental data 360 can include measurements related to ambient conditions (temperature and relative humidity) that impact the skin's shear properties further exacerbating the individual's susceptibility to pressure ulcers. The coefficient of friction is another parameter that can be measured at an interface as described herein. Capturing and storing these measurements, e.g., pressure 354 and moisture 357, in the data store 312 allows alerting or triggering an intervention based on a measurement of the pressure 354 or the moisture 357 or a composite assessment of two or more measured parameters.

The machine learning model data 348 can correspond to data for one or more machine learning models used to ascertain various thresholds for prevention of a pressure ulcer and where an automated intervention 333, automated intervention 336, or manual intervention 339 should be alerted or triggered. Thresholds can for example be based on the pressure 354, moisture 357, and/or environmental data 360. Also, a camera or other image acquisition device can be employed to take a picture of one or more interface(s) between an individual and the wheelchair 321 or the other equipment 324 to allow the system 100 to assess the condition of the interface(s) and make a determination.

Machine learning model data 348 can also help determine risk of pressure ulcers based on correlations between sensor data 342 and individual data 345. Individual data 345 relates to an individual who may be at risk for a pressure injury at the interface between the individual and the wheelchair 321 or the other equipment 324. For example, the Braden Scale for Predicting Pressure Sore Risk describes a clinical assessment that includes Sensory Perception, Moisture, Activity, Mobility, Nutrition, and Friction and Shear associated with an individual who may be at risk for a pressure sore. Machine learning model data 348 can combine data from the sensor data 342 with the individual's electronic medical record (EMR) 363 and a personal health record (PHR) 366 to determine correlation between a pressure ulcer and various data, such as nutrition, that may be present in the EMR 363 or the PHR 366.

Individual data 345 also includes device configuration 369 which relates to configuration of one or more devices associated with the wheelchair 321 or the other equipment 324. For example, the computing device 303 can use the device configuration data 369 to configure the application 315 running on the computing device 306 (e.g., a smartphone, a tablet, or a laptop) to receive from the fabric-based sensing component 327, 330 and wirelessly (e.g., using Bluetooth® or Zigbee® protocols) trigger the automated intervention 333, automated intervention 336, or manual intervention 339. Device configuration data 369 can include configurations based on Apple's ResearchKit® open source software to facilitate integration with HealthKit®.

In some embodiments, the computing device 306 will process measurements obtained from fabric-based sensing component 327, 330 and determine whether to trigger an automated intervention 333, automated intervention 336, or alert a manual intervention 339. In some example embodiments, a single-board computer or an inexpensive processor can be used for signal processing. The manual intervention 339 can be sent to the computing device 306 (e.g., a smartphone, a tablet, or a laptop) associated with the individual or caregiver. The caregiver data 351 is stored to allow the system 100 to alert a caregiver to intervene, such as through manual intervention 339 (e.g., reposition an individual who may be at risk for a pressure ulcer). The manual intervention can require that the caregiver enter into the system the manual intervention action taken by the caregiver in response to the alert. This can take the form of the caregiver providing a description of the nature of the manual intervention given and entering it into the system. It can also take the form of requiring that the caregiver photograph the area of the individual that is the subject of the alert and capturing the photograph into the system.

The analytics application 318 provides an easy-to-use platform or information infrastructure to acquire the data to carry out "Big Data" analytics. The analytics application 318 can apply machine learning techniques to machine learning model data 348 stored in the data store 312. The analytics application 318 can develop strategies to anticipate the formation of pressure ulcers and thereby avoid them. The analytics application 318 can also further the design (redesign and/or modification) of equipment (wheelchairs, prosthetics, cribs, beds, neck braces, automobile seats, etc.) for individuals. For example, applying machine learning techniques to the machine learning model data 348 stored in the data store 312 can provide the foundational data for enhancing the design of the equipment. Another aspect of the analytics application 318 can be to create an index for degree of comfort of seating, which can be based on data stored in the data store 312, and can provide an objective index of seating comfort.

The computing device 306 is representative of a plurality of devices that can be coupled to the network 309. The computing device 306 can comprise, for example, a processor-based system such as a computer system. Such a computer system may be embodied in the form of a desktop computer, a laptop computer, personal digital assistants, cellular telephones, smartphones, web pads, tablet computer systems, or other devices with like capability. The computing device 306 may include a display 378. The display 378 can comprise, for example, one or more devices such as liquid crystal display (LCD) displays, gas plasma-based flat panel displays, organic light emitting diode (OLED) displays, electrophoretic ink (E ink) displays, LCD projectors, or other types of display devices, etc.

The computing device 306 can be configured to execute various applications such as a caregiver application 372 and/or other applications such as an automatic intervention. The caregiver application 372 can be executed in a computing device 306, for example, to access network content served up by the computing device 306 and/or other servers, thereby rendering a user interface 375 on the display 378. To this end, the caregiver application 372 can comprise, for example, a browser, a dedicated application, etc., and the user interface 375 can comprise a network page, an application screen, etc. The computing device 306 can be configured to execute applications beyond the caregiver application 372 such as, for example, clinical application, word processors, spreadsheets, and/or other applications.

Caregiver application 372 or UI 375 can display for example the pressure 354 and/or moisture 357 over time along with the environmental data 360 (e.g., changing ambient conditions). One or more manual intervention 339 can be rendered on the display 378. The manual intervention 339 can also vibrate the computing device 306 or send an audio alarm so that the individual (or caregiver) can take the appropriate intervention to prevent the formation of a pressure ulcer.

The system 100 can also be used to develop a knowledge base for design of SCI aids. The data stored in the data store 312 of the system 100 can be processed and analyzed using machine learning algorithms. A knowledge base of rules establishing the relationship between the real-world data collected by the system 100 when using a wheelchair and its design can be developed applying the principles of knowledge engineering to develop knowledge-based decision support systems. The system 100 data and the knowledge base rules can be used for enhancing the design (and performance) of current generation of aids by equipment manufacturers (e.g., wheelchairs, beds, etc.). As described, the system 100 allows data to be acquired and analyzed from spinal cord injury individuals—both in real-time and over long periods of time—to better understand the individual's requirements and to enhance the design and performance of the current generation of assistance devices/equipment, such as wheelchairs and prosthetics.

Figure 4B:
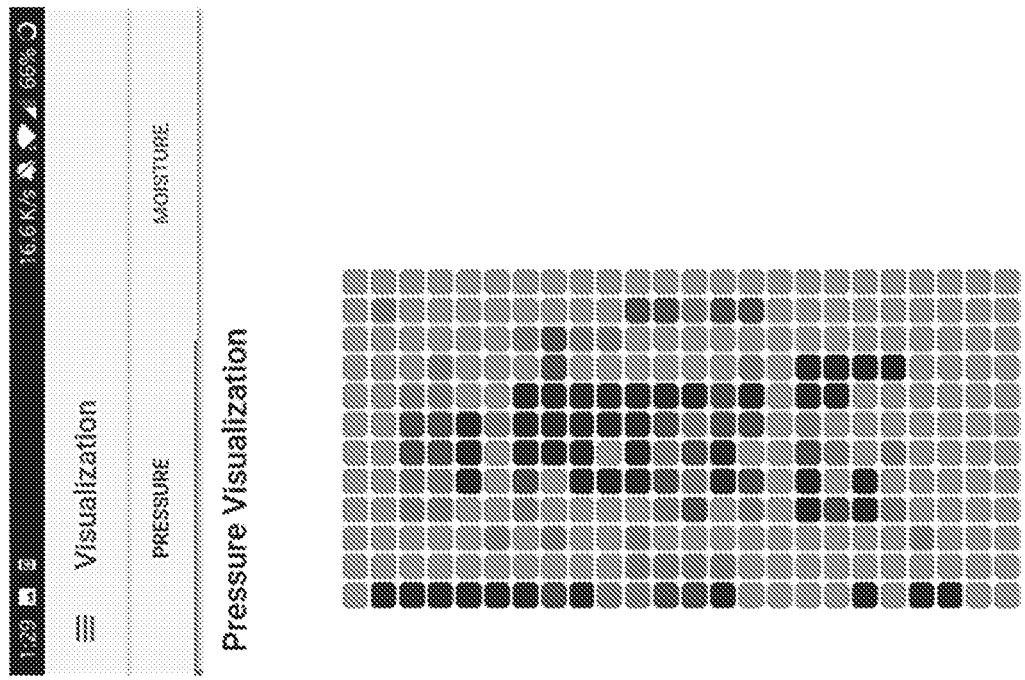
FIG. 4B depicts an exemplary user interface showing an intensity based on pressure rendered in a 12×24 grid.
Figure 4A:
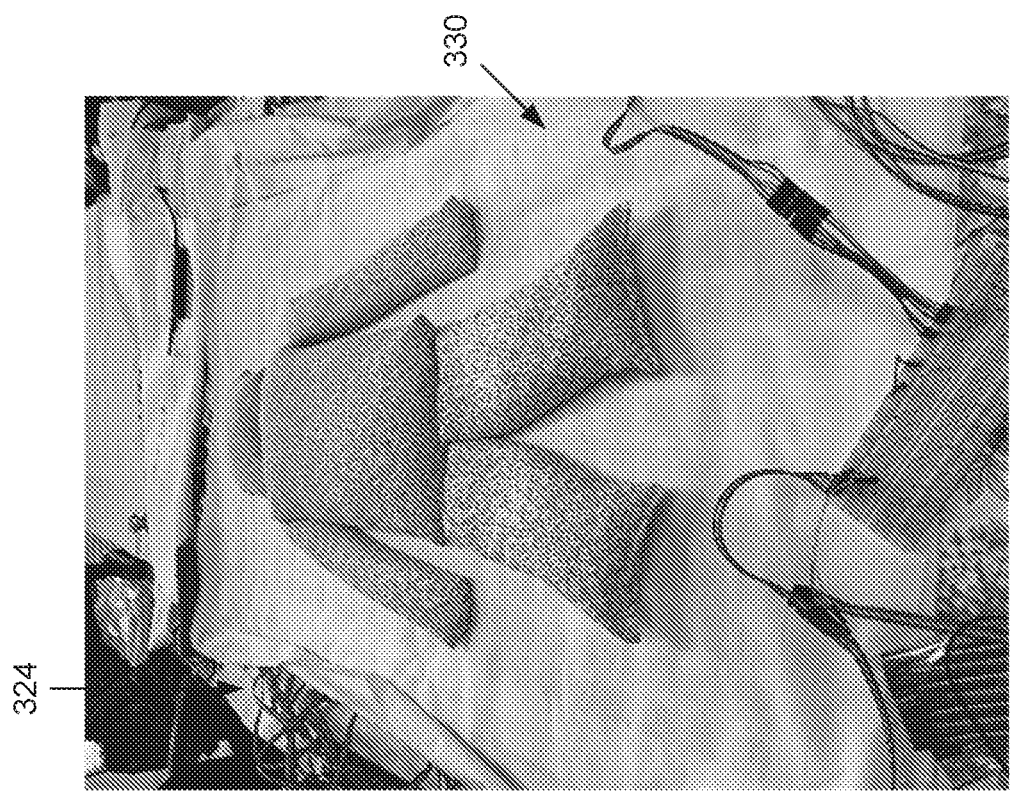
FIG. 4A depicts an exemplary of a fabric-based sensor that is configured to be between an individual and equipment of the present disclosure.

FIG. 4A depicts an example of a pressure sensing component of a fabric-based sensing component 330 that is between an individual and other equipment 324. The example of the fabric-based sensing component 330 shown includes a pressure sensing component with three layers. The pressure sensing component measures pressure where two high conductive fabrics make contact through a low conductive (high resistive) fabric. The fabric-based sensing component can be seen in FIG. 4A as a plurality of one-inch squares.

In FIG. 4A it may be noticed that the arrangement of sensors forms a 24×12 fabric-based sensor network within the fabric-based sensing component 330 with corresponding data buses. Each row has 12 sensors (again, the one-inch squares depicted in FIG. 4A). While 12 sensors are depicted, the number of sensors implemented can be more or less than 12. Similarly, the data bus can vary. A conductive textile fiber/yarn (e.g., metal-clad nylon or aramid, or stainless steel) allows each row of sensors to be connected to the system 100 (FIG. 3) which includes the network 309 (FIG. 3). While any textile fabric can be used, the fabric-based sensing component 330 shown was created using knitted fabric. Knitted fabric can stretch and provide a good recovery rate.

The fabric-based sensing component 330 can also include a moisture sensing component. The moisture sensing component can include a high conductive material which is a woven fabric. The moisture sensing component can be configured similarly as the pressure sensing component, for example the arrangement of sensors can form a 24×12 sensor array. The moisture sensing component can have two layers. The moisture sensing component for example can measure moisture where two layers of conductive fabrics make contact through moisture between the layers. As with the pressure sensing component, the number of sensors and the data bus of the moisture sensing component can vary.

FIG. 4B depicts an example user interface 450 showing an intensity based on pressure measurements rendered in a 12×24 grid or array. The user interface 450 is an example of the system 100 causing the computing device 306 to render the UI 375. In this example, an intensity based on pressure 354 is rendered in a 12×24 grid corresponding to aggregated measurements from a fabric-based sensing component 330 associated with other equipment 324 (FIG. 4A). In some examples, the user interface 450 can be used by an individual to visualize what is happening to him or her when sitting in the wheelchair 321 (FIG. 3) or when in contact with a surface of other equipment 324.

Figure 5:
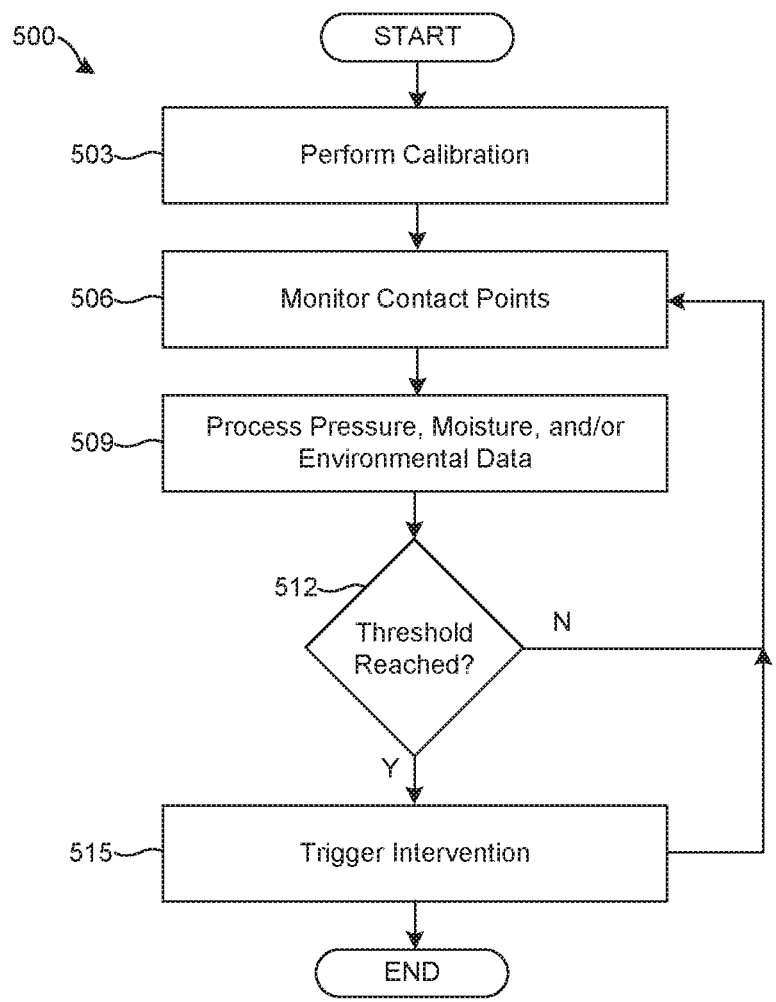
FIG. 5 shows an exemplary flow chart of a prevention system of the present disclosure.

With reference to FIG. 5, shown is a flowchart 500 that shows steps of a method implemented by the system 100. Alternatively, FIG. 5 provides one example of the execution of the application 315 for detecting, alleviating or slowing and/or preventing the formation of a pressure ulcer in accordance with various embodiments of the present disclosure. FIG. 5 can also be seen as an example flowchart 500 for a processor on a single board computer for a system 100 for detecting, alleviating or slowing and/or preventing the formation of a pressure ulcer in accordance with various embodiments of the present disclosure.

Accordingly, at box 503, the system 100 can perform a calibration process for detecting, alleviating or slowing and/or preventing the formation of a pressure ulcer. For example, the application 315 of the system 100 can use a calibration process to obtain reference points (e.g., a hardness) for the wheelchair 321 or the other equipment 324. Weights of the fabric-based sensing component 327, 330, or their pressure sensing components and moisture sensing components can also be obtained. Alternatively, the weight of the moisture sensing component, or any other weight, can be obtained periodically. The system 100 can also set a threshold for risk of pressure injury. For example, the application 315 can set a defined duration and degree of pressure 354 (or moisture 357) below which the risk of pressure injury is deemed to be acceptable. The threshold can also account for environmental data 360.

At box 506, the system 100 can monitor contact points by obtaining pressure 354, moisture 357, or environmental data 360 from the fabric-based sensing component 327, 330. The application 315 can monitor the fabric-based sensing component 327, 330 as calibrated in box 503. Accordingly, with the fabric-based sensing component 327, 330 in place on the wheelchair 321 or the other equipment 324, the contact points between the individual and the wheelchair 321 or the other equipment 324 can be sensed. In this way, the application 315 can obtain from the fabric-based sensing component 327, 330 a measurement that corresponds with an individual's risk of pressure injury.

At box 509, the application 315 can process pressure 354, moisture 357, or environmental data 360 obtained from the fabric-based sensing component 327, 330. The processing can for example aggregate pressure 354 to identify a body part affected. In other examples, the processing can use a weight of the moisture sensing component to increase a threshold for the pressure 354.

At box 512, the application 315 can determine whether the threshold is reached. For example, if the fabric-based sensing component 327, 330 detects a measurement that is above a threshold or threshold value defined in box 503 or box 509, this condition can be associated with an individual who is at risk for a pressure injury. The application 315 can determine that the individual is at risk for a pressure injury due for example to an assessment of pressure 354, moisture 357, environmental data 360 or a composite assessment of two or more of the data. If the application 315 determines that the individual is at risk for a pressure injury, the process continues to box 515.

If the application 315 determines that the threshold has not been reached, this condition can be associated with an individual who is not currently at risk for a pressure injury. The application 315 can for example determine that a Braden scale score associated with the individual is below a threshold, or that a duration and degree of pressure 354 (or moisture 357) is below the threshold.

The application 315 can also use fabric-based sensing component 327, 330 to determine that the individual has recently been repositioned. Further, the application 315 can adjust the threshold based on individual data 345 such as the EMR 363 or the PHR 366. In this way, the application 315 can use non-time based factors to determine whether the threshold has been reached, and does not have to determine that a threshold has been reached based on whether the individual has been repositioned within a fixed amount of time (e.g., 15 minutes or two hours in some protocols). If the threshold is not reached, then the process can return to box 506. Alternatively, in some implementations, the process can end if the threshold is not reached or the individual is determined to not be at risk for a pressure injury.

At box 515, the application 315 can trigger the automated intervention 333, automated intervention 336, or alert a manual intervention 339. The application 315 can activate actuators to actively control portions of the wheelchair 321 or the other equipment 324. The automated intervention 333, 336 can also be triggered to turn on one or more fans to ventilate contact surface points associated with the wheelchair 321 or the other equipment 324.

The manual intervention 339 can also include an instruction for a caregiver to take a picture of an interface area (or a body party of the individual). The application 315 can receive the picture and store the picture in the data store 312, such as in individual data 345. The application 315 can determine, for example based on the picture and the data stored in the sensor data 342, that it is unnecessary for a wound specialist to physically visit the individual. An alert can also be sent that requires a confirmation by a caregiver, for example to be entered into and stored within the system 100. The application 315 can prevent the caregiver from acknowledging the alert when values of pressure 354 indicate the pressure has not been removed and/or based on the application 315 determining that an appropriate picture has not been received in the data store 312. In some embodiments, the system 100 can render a user interface to allow the wound specialist to view the picture, monitor the condition of the skin, and view and/or update assessments (e.g., Braden scale), and permit the wound specialist to refrain from physically visiting the individual. Thereafter, the process can return to box 506. Alternatively, in some implementations, the process can proceed to completion.

Figure 6:
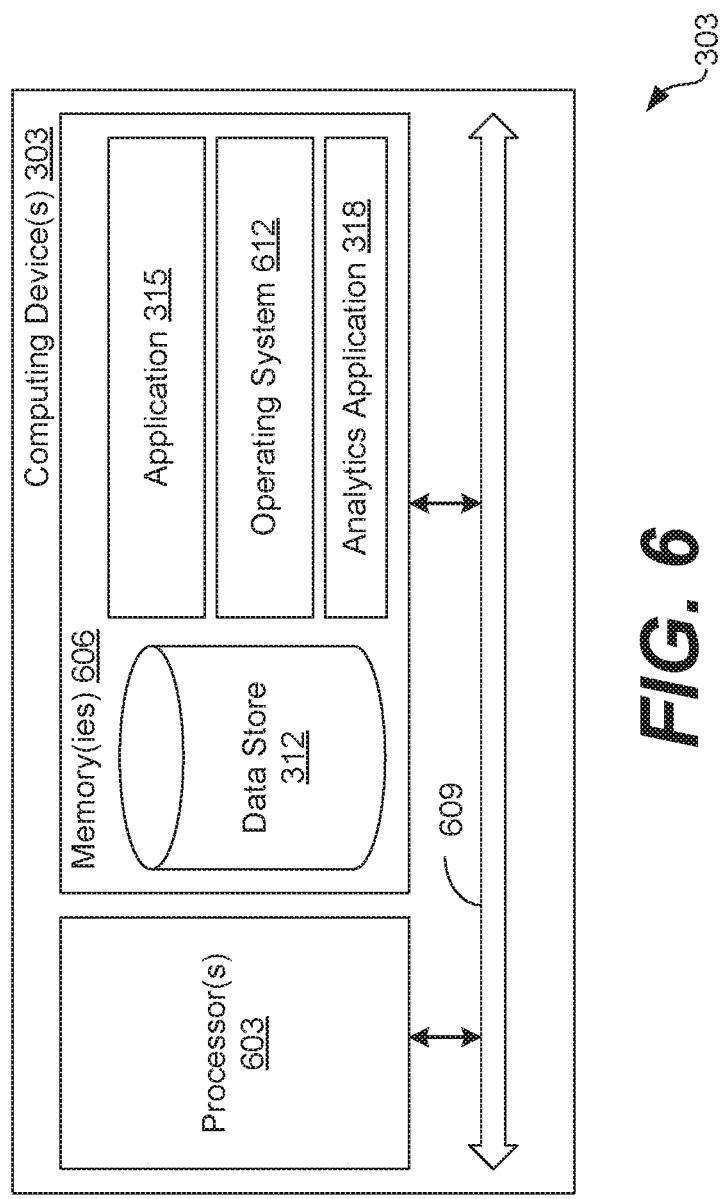
FIG. 6 is a schematic diagram of an example of a computing device used to implement a prevention system of the present disclosure.

With reference to FIG. 6, shown is a schematic block diagram of a computing device 303 that can be used to implement the system 100 of FIG. 3 according to various embodiments of the present disclosure. The computing device 303 includes at least one processor circuit, for example, having a processor 603 and a memory 606, both of which are coupled to a local interface 609. To this end, the computing device 303 can comprise, for example, at least one server computer or like device. The local interface 609 can comprise, for example, a data bus with an accompanying address/control bus or other bus structure as can be appreciated.

The computing device 303 can include an input/output device such as a display. The input/output device can comprise, for example, one or more devices such as a keyboard, mouse, gesture input device, touch screen (resistive, capacitive, or inductive), microphone, liquid crystal display (LCD) display, gas plasma-based flat panel display, organic light emitting diode (OLED) display, projector, or other types of input/output device, etc.

Stored in the memory 606 are both data and several components that are executable by the processor 603. In particular, stored in the memory 606 and executable by the processor 603 can be a application 315, an analytics application 318, and an operating system 612, and/or other applications. Also stored in the memory 606 can be a data store 312 and other data. The computing device 303 can also include one or more converter(s) to interface with cameras and/or system peripherals.

It is understood that there can be other applications that are stored in the memory 606 and are executable by the processor 603 as can be appreciated. For example, applications can include Apple's ResearchKit® open source software to facilitate integration with HealthKit® and take advantage of the wellness and healthcare ecosystem offered by the iOS platform. Examples of the system 100 can be implemented on the iOS platform, the Android platform, or various other operating system 612 as can be appreciated.

Where any component discussed herein is implemented in the form of software, any one of a number of programming languages can be employed such as, for example, C, C++, C#, Objective C, Java®, JavaScript®, Perl, PHP, Visual Basic®, Python®, Ruby, Delphi®, Flash®, or other programming languages.

A number of software components are stored in the memory 606 and are executable by the processor 603. In this respect, the term "executable" means a program file that is in a form that can ultimately be run by the processor 603. Examples of executable programs can be, for example, a compiled program that can be translated into machine code in a format that can be loaded into a random access portion of the memory 606 and run by the processor 603, source code that may be expressed in proper format such as object code that is capable of being loaded into a random access portion of the memory 606 and executed by the processor 603, or source code that may be interpreted by another executable program to generate instructions in a random access portion of the memory 606 to be executed by the processor 603, etc. An executable program can be stored in any portion or component of the memory 606 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 606 is defined herein as including both volatile and nonvolatile memory and data storage components. Volatile components are those that do not retain data values upon loss of power. Nonvolatile components are those that retain data upon a loss of power. Thus, the memory 606 can comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM can comprise, for example, static random access memory (SRAM), dynamic random access memory (DRAM), or magnetic random access memory (MRAM) and other such devices. The ROM can comprise, for example, a programmable read-only memory (PROM), an erasable programmable read-only memory (EPROM), an electrically erasable programmable read-only memory (EEPROM), or other like memory device.

Also, the processor 603 can represent multiple processors 603 and the memory 606 can represent multiple memories 606 that operate in parallel processing circuits, respectively. In such a case, the local interface 609 can be an appropriate network that facilitates communication between any two of the multiple processors 603, between any processor 603 and any of the memories 606, or between any two of the memories 606, etc. The local interface 609 can comprise additional systems designed to coordinate this communication, including, for example, performing load balancing. The processor 603 can be of electrical or of some other available construction.

Although the application 315, analytics application 318, caregiver application 372, and other various systems described herein can be embodied in software or code executed by general purpose hardware as discussed above, as an alternative the same can also be embodied in dedicated hardware or a combination of software/general purpose hardware and dedicated hardware. If embodied in dedicated hardware, each can be implemented as a circuit or state machine that employs any one of or a combination of a number of technologies. These technologies can include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Although the flowchart of FIG. 5 shows a specific order of execution, it is understood that the order of execution can differ from that which is depicted. For example, the order of execution of two or more blocks can be scrambled relative to the order shown. Also, two or more blocks shown in succession in FIG. 5 can be executed concurrently or with partial concurrence. Further, in some embodiments, one or more of the blocks shown in FIG. 5 can be skipped or omitted (in favor, e.g., conventional pressure injury risk mitigation approaches). In addition, any number of counters, state variables, warning semaphores, or messages can be added to the logical flow described herein, for purposes of enhanced utility, accounting, performance measurement, or providing troubleshooting aids, etc. It is understood that all such variations are within the scope of the present disclosure.

Also, any logic or application described herein, including the application 315, analytics application 318, caregiver application 372 that comprises software or code can be embodied in any non-transitory computer-readable medium for use by or in connection with an instruction execution system such as, for example, a processor 603 in a computer system or other system. In this sense, the logic can comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium can be a random access memory (RAM) including, for example, static random access memory (SRAM) and dynamic random access memory (DRAM), or magnetic random access memory (MRAM). In addition, the computer-readable medium can be a read-only memory (ROM), a programmable read-only memory (PROM), an erasable programmable read-only memory (EPROM), an electrically erasable programmable read-only memory (EEPROM), or other type of memory device.

Figure 7:
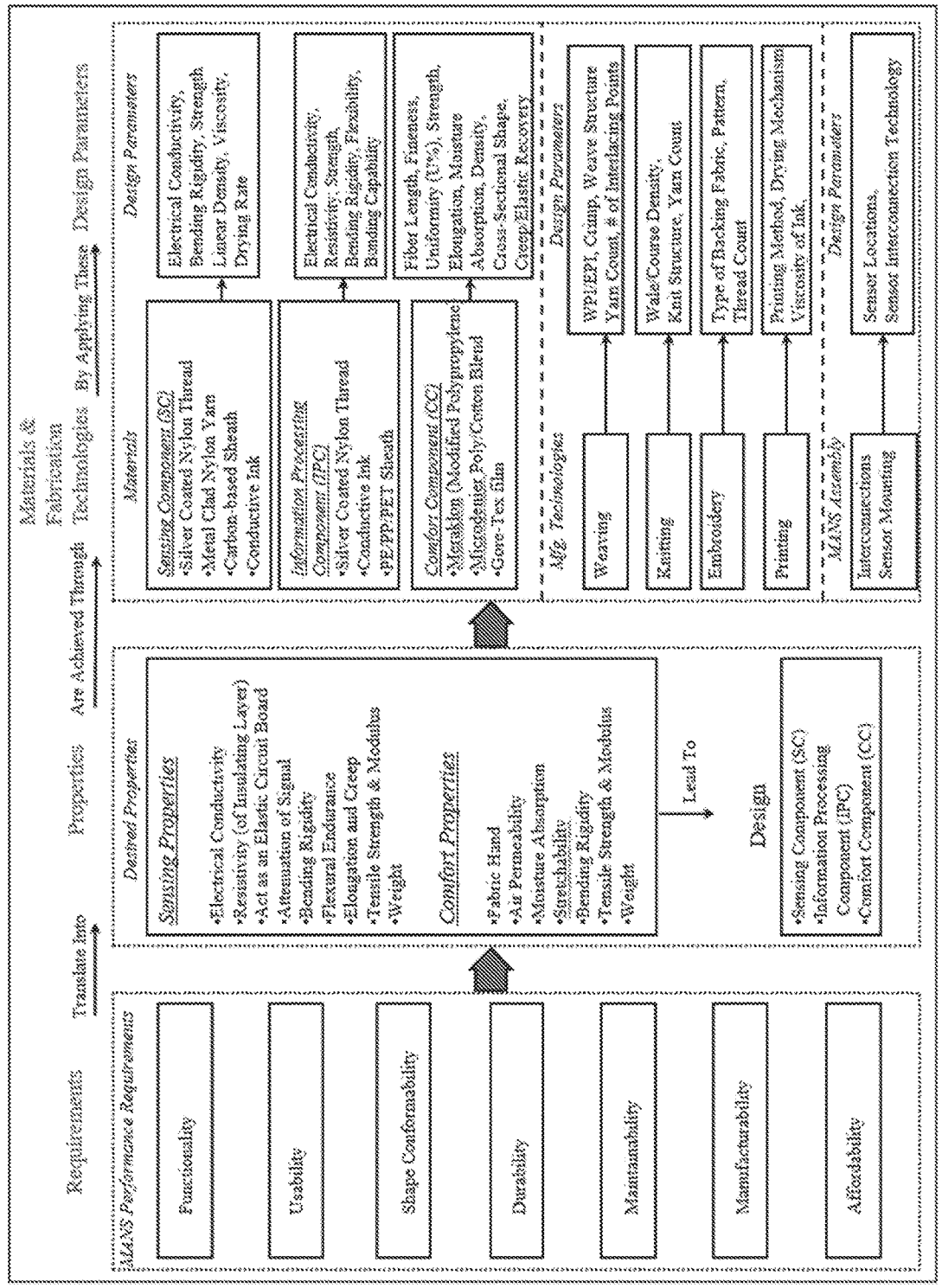
FIG. 7 shows a design and development framework for a prevention system of the present disclosure.

Referring now to FIG. 7, shown is a design and development framework for the system 100. As shown at the top of FIG. 7, performance requirements of the fabric-based sensor network have been identified. These requirements are translated into appropriate Properties of the system 100: Sensing and Comfort properties. The Properties lead to the specific Design for the sensing technology: an integrated structure meeting the primary requirements of sensing, information processing, and comfort. The desired Properties in the Design are achieved through the appropriate choice of Materials & Fabrication Technologies by applying the corresponding Design Parameters as shown in the figure. These major facets in the proposed framework are linked together as shown by the arrows between the dotted boxes in FIG. 7. The use of this framework for the development of system 100 is illustrated with the design of the unit cell 103 (FIGS. 1 & 2) of the fabric-based sensing component 327, 330 (FIG. 3).

FIG. 7 depicts several example materials properties of the system 100. Fabric-based sensing component 327, 330 can be composed of silver coated nylon thread, metal clad nylon or aramid yarn, carbon-based sheath, and conductive ink. Information processing components of the system 100 can be composed of silver coated nylon thread, conductive ink, and/or plastic such as Polyethylene (PE)/Polypropylene (PP)/Polyethylene terethalate (PET). Fabric-based sensing component 327, 330 can include a comfort component of meraklon (Modified Polypropylene), Microdenier Poly/Cotten Blend, and/or Gore-Tex film.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

We claim:

1. A pressure ulcer system, comprising:
    a fabric-based sensing component having a distributed sensor network formed of an addressable array of a plurality of fabric patches that define pressure sensors configured to detect pressure at an interface location between an individual and a surface with which the individual is in contact through the fabric-based sensing component, wherein the addressable array of the plurality of pressure sensors are interconnected by a conductive yarn data bus within the fabric-based sensing component to form a plurality of sensing unit cells, the addressable array of the plurality of pressure sensors forming a pressure sensing layer that is formed solely of fabrics as sensing elements, wherein each of the plurality of pressure sensors is defined by two high conductive fabrics having a resistivity value between about 0.002 and about 8 ohms per square, each of the high conductive fabrics being integrated with the conductive yarn data bus by weaving, knitting, embroidery, or sewing, and configured to make electrical contact through a low conductive fabric having a resistivity value between about 10E3 and about 10E13 ohms per square, wherein the addressable array of the plurality of pressure sensors provide a pressure value for each of a plurality of respective locations in the fabric-based sensing component; and
    a computing device;
    wherein the fabric-based sensing component is configured to transmit the measure of pressure to the computing device, wherein the computing device is configured to
       determine, based on an assessment of duration and/or intensity of pressure, using the measured pressure value at the array of sensors, that an individual is at risk for developing a pressure ulcer at an interface location between the individual and a surface with which the individual is in contact through the fabric-based sensing component; and
       in response to determining the duration and/or intensity of the pressure exceeding a designated threshold value or values for at least one sensing location of the plurality of sensing locations at the interface location, alerting a manual intervention or triggering an automated intervention based on the measured pressure value.

2. The system of claim 1, wherein the computing device, is configured via program instructions, to obtain, from the fabric-based sensing component, at least one measurement corresponding to at least one of: a pressure value associated with at least one contact point between the individual and the surface through the fabric-based sensing component at the interface location, wherein the at least one measurement is stored in a data store for storing electronic medical records.

3. The system of claim 2, further comprising:
    the data store;
    the program instructions further causing the computing device to store the at least one measurement in the data store; and
    wherein the system further comprises:
       an analytics system configured, via program instructions, to apply machine learning operations to the at least one measurement to (i) create a knowledge base for anticipating and avoiding formation of pressure ulcers or (ii) provide an index for degree of comfort of seating.

4. The system of claim 1, wherein the fabric-based sensing component is configured via sensors to obtain a reading of an environmental condition.

5. The system of claim 1, wherein the fabric-based sensing component is formed as a shape-conformable structure for a chair, crib, bed, body brace, body cast, wheelchair, or equipment for supporting a body or a body part of the individual, and the fabric-based sensing component is positionable between the individual and the chair, crib, bed, body brace, body cast, wheelchair, or equipment.

6. The system of claim 1, wherein the plurality of pressure sensors comprise at least one of a silver-coated nylon thread, a metal-clad nylon, a metal-clad aramid yarn, or a carbon-based sheath.

7. The system of claim 1, wherein the plurality of pressure sensors comprise a textile material comprising at least one of cotton, nylon, Polyethylene (PE), Polypropylene (PP), Polyethylene terephthalate (PET) yarn or fabric, wherein the textile material is configured with a conductive surface comprising conductive ink.

8. The system of claim 1, wherein the addressable array of a plurality of pressure sensors includes (i) a first set of sensors having a first set of sensor density at a first location and (ii) a second set of sensors having a second set of sensor density at a second location.

9. The system of claim 1, wherein the computing device is configured to direct the alert for manual intervention, wherein the alert requires a caregiver acknowledge the alert by entering a response.

10. The system of claim 1, wherein the computing device is configured to direct the triggering of an automated intervention when specific thresholds of pressure, duration, environmental data, and/or calculated composite measurements are reached.

11. The system of claim 1, wherein the conductive fabrics are integrated into either (i) a textile fabric of at least one of a knitted fabric or a woven fabric or (ii) metamaterial comprising a thin foil or film.

12. The system of claim 1, wherein a single conductive fiber connection of the conductive yarn data bus is configured to merge more than one signal measured by the plurality of pressure sensors.

13. The system of claim 1, further comprising a second addressable array of a plurality of fabric patches that define moisture sensors configured to detect moisture at an interface location between the individual and the surface with which the individual is in contact through the fabric-based sensing component, wherein the addressable array of the plurality of moisture sensors form a moisture sensing layer that is formed of fabrics as sensing elements, wherein each of the plurality of moisture sensors is defined by two conductive fabrics placed adjacent to each other such that when moisture passes from one of the conductive fabrics to the other of the conductive fabrics, the moisture closes a circuit between the fabrics to provide a moisture value for each of a plurality of respective locations in the fabric-based sensing component, and wherein the moisture sensing layer is located at a first layer to be in proximal contact with the individual, and wherein the pressure sensing layer is located at a second layer in distal contact with the individual.

* * * * *